(12) United States Patent
Matousek et al.

(10) Patent No.: US 8,248,600 B2
(45) Date of Patent: Aug. 21, 2012

(54) RAMAN DETECTION OF CONTAINER CONTENTS

(75) Inventors: Pavel Matousek, Abingdon (GB); Eva Charlotte Eliasson, Bergen (NO)

(73) Assignee: The Science and Technology Facilities Council, Oxfordshire (GB)

( * ) Notice: Subject to any disclaimer, the term of this patent is extended or adjusted under 35 U.S.C. 154(b) by 95 days.

(21) Appl. No.: 12/516,170

(22) PCT Filed: Nov. 21, 2007

(86) PCT No.: PCT/GB2007/004452
§ 371 (c)(1),
(2), (4) Date: May 22, 2009

(87) PCT Pub. No.: WO2008/062185
PCT Pub. Date: May 29, 2008

(65) Prior Publication Data
US 2010/0053606 A1    Mar. 4, 2010

(30) Foreign Application Priority Data
Nov. 24, 2006  (GB) .................................. 0623511.3

(51) Int. Cl.
*G01J 3/44* (2006.01)
(52) U.S. Cl. ...................................................... 356/301
(58) Field of Classification Search .................. 356/301, 356/72–73
See application file for complete search history.

(56) References Cited

U.S. PATENT DOCUMENTS

| | | | |
|---|---|---|---|
| 4,645,340 A | 2/1987 | Graham et al. | |
| 4,784,486 A | 11/1988 | Van Wagemen et al. | |
| 5,506,678 A | 4/1996 | Carlsen et al. | |
| 6,975,891 B2 * | 12/2005 | Pawluczyk | 600/310 |
| 2004/0263843 A1 | 12/2004 | Knopp et al. | |
| 2006/0121442 A1 | 6/2006 | Perraut et al. | |
| 2006/0146384 A1 * | 7/2006 | Schultz et al. | 359/9 |

FOREIGN PATENT DOCUMENTS

| | | |
|---|---|---|
| CN | 1584555 A | 2/2005 |
| GB | 1171689 | 11/1969 |
| GB | 1510827 | 5/1978 |
| JP | 9-127001 A | 5/1997 |
| JP | 2005070009 | 3/2005 |

OTHER PUBLICATIONS

Eliasson et al., "Noninvasive Detection of Concealed Liquid Explosives Using Raman Spectroscopy", Anal. Chem, 2007, vol. 79, pp. 8185-8189.

(Continued)

*Primary Examiner* — Tarifur Chowdhury
*Assistant Examiner* — Abdullahi Nur
(74) *Attorney, Agent, or Firm* — Birch, Stewart, Kolasch & Birch LLP

(57) ABSTRACT

Methods and apparatus for screening the unknown contents of containers using Raman spectroscopy are disclosed, especially for security screening applications such as in airports. A probe light beam is directed through the wall of a container to a sample region within the container contents. Light scattered out of the beam within the sample region is collected along a path which passes through a separate part of the container wall, for Raman spectral analysis.

45 Claims, 11 Drawing Sheets

OTHER PUBLICATIONS

Eliasson et al., "Non-invasive detection of cocaine dissolved in beverages using displaced Raman spectroscopy", Analytica Chimica Acta, vol. 607, No. 1, Nov. 19, 2008, pp. 50-53.

Matousek., "Inverse Spatially Offset Raman Spectroscopy for Deep Noninvasive Probing of Turbid Media", XP009096202, Applied Spectroscopy, vol. 60, No. 11, Nov. 1, 2006, pp. 1341-1347.

Matousek et al., "Noninvasive Raman Spectroscopy of Human Tissue In Vivo", XP009096205, Applied Spectroscopy, vol. 60, No. 7, Jul. 2006, pp. 758-763.

Coates., "Molecular Spectroscopy Workbench New technologies for Process Analytical and Quality Control Applications: Compact Raman", Spectroscopy, Advanstar Communications, US, vol. 21, No. 2, Feb. 2006, pp. 68-74.

Lewis et al., Raman spectroscopic studies of explosive materials: towards a fieldable explosives detector, XP-002469739, Spectrochimica Acta Part A, vol. 51A, No. 12, Nov. 16, 1995, pp. 1985-2000.

Carter et al., Raman Spectroscopy for the in Situ Identification of Cocaine and Selected Adulterants, Applied Spectroscopy, vol. 54, No. 12, Dec. 2000, pp. 1876-1881.

Volumetric Raman Microscopy Through a Turbid Medium, Brenan CJH and Hunter I W, J Raman Spectroscopy 27, p. 561, 1996.

Time-resolved fluorescence and photon migration studies in biomedical and model random media, Das B.B., Liu F. and Alfonso R.R., Rep. Prog. Phys. 60, p. 227, 1997.

* cited by examiner

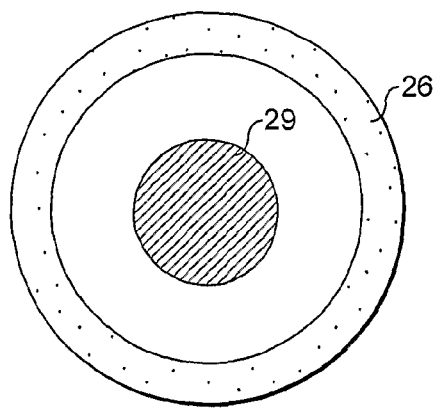
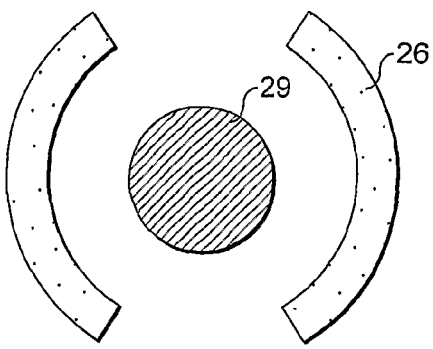
FIG. 4a    FIG. 4b
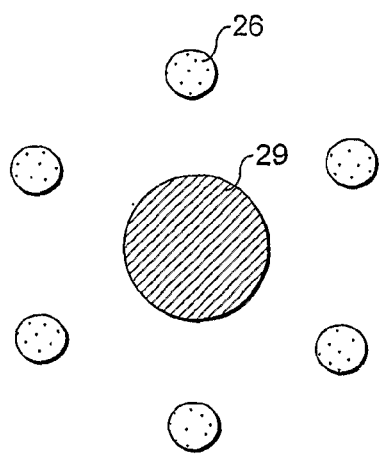
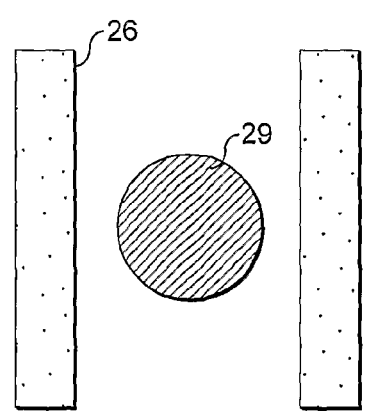
FIG. 4c    FIG. 4d
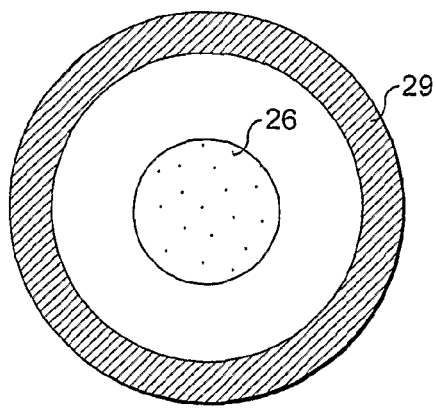
FIG. 4e

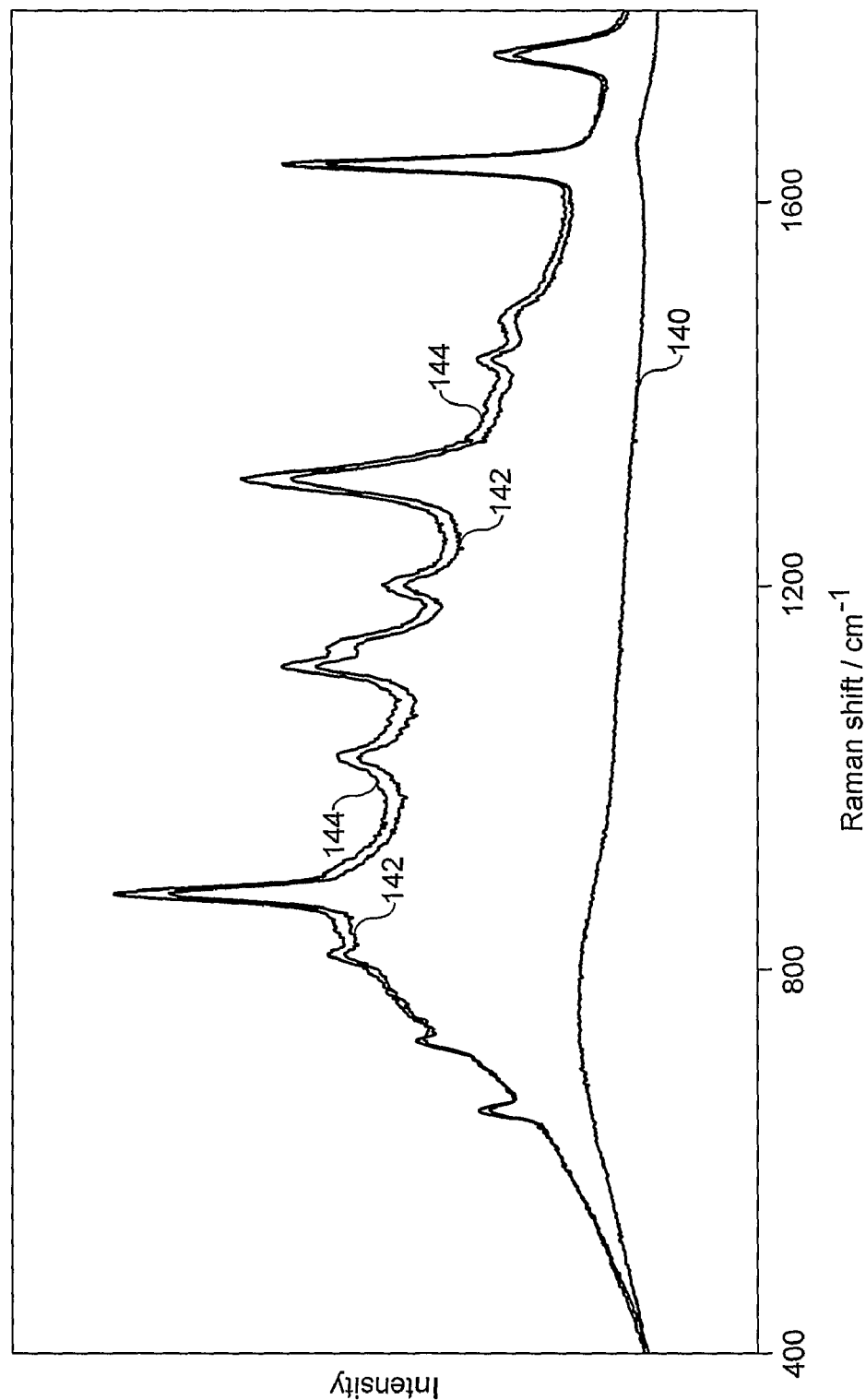

RAMAN DETECTION OF CONTAINER CONTENTS

FIELD OF THE INVENTION

The present invention relates to methods and apparatus for determining characteristics of the contents of containers using Raman spectral techniques, especially in circumstances when the contents of the container are unknown such as in security screening applications.

BACKGROUND OF THE INVENTION

Recent events and a perceived increased threat from terrorist activities have resulted in an increased need to be able to screen the contents of bottles and similar containers which passengers may wish to carry onto an aeroplane or into a similar security sensitive environment. Such screening should be able to identify whether the contents of a container pose a threat to security, for example containing substances which could be ingredients for explosives, toxic, or otherwise unauthorised. Moreover, such screening needs to be rapid, avoiding taking samples out of relevant containers while still providing accurate results and a very low incidence of false alarms.

Raman spectroscopy is a known technique for determining characteristics or composition of materials, and has excellent chemical sensitivity, although is largely restricted to measurements of surface materials. Raman scattering occurs when a photon is inelastically scattered within a medium, changing the frequency of the photon by typically a few hundred to a few thousand cm−1 according to a spectrum characteristic of the scattering material. Although chemically specific, Raman scattering is very weak, and the spectral signal is easily swamped by fluorescence. In the case of the contents of a glass, or especially a plastic container, the relatively weak Raman signature of the typically liquid contents is often likely to be badly swamped by the much stronger signature of the container.

There are many other applications in which Raman spectral determination of characteristics within a container would be beneficial, but are at present hampered by the above problems, including for example the determination of beverage content, especially alcohol content, either on a production line or in a production, distribution or retail context.

The invention seeks to address the problems of the related prior art.

SUMMARY OF THE INVENTION

Aspects of the invention provide an effective solution for non-invasive security screening of liquids or gels for explosives and other harmful substances at airports and other sensitive facilities and installations. Raman spectroscopy gives highly specific chemical information in a manner similar to infra red spectroscopy, but at optical frequencies, rapidly and without absorption problems with water. The invention permits Raman spectroscopy measurements of the contents of unopened plastic containers to be made. However, although bottles are described herein as an example of the invention being applied, the technique is widely applicable, for example being useful for detecting compositional information of gels and other forms of material in transparent and semi-transparent containers.

Generally, the invention provides a method of probing the contents, especially liquid or gel contents which are transparent or semi transparent such as beverages and cosmetics, of a container, such as a plastic bottle or tube, by directing probe light through the container wall into the contents. Light scattered out of the beam within the contents is collected, and Raman spectral features in the scattered light are detected to determine characteristics of the contents. The wall of the container may frequently be a much stronger source of Raman scattering than the contents of the container, as well as a strong source of fluorescence and other light which may reduce the sensitivity of the technique to the characteristics of the contents. The light scattered out of the beam is therefore collected along an optical pathway or beam which avoids intersection with the container wall in the same region as the probe light.

The probe light beam is preferably one or more beams of laser light, and the scattered light may be collected using a variety of optical arrangements, for example using optics having one or more focal points or regions coincident with or containing a portion of the probe light beam or beams within the contents. In particular, the collection optics may act to image the sample region, for example onto the end of a fibre optic bundle for delivery to a spectrograph.

Concentric probe and collection beams, and fragmented beams in various configurations may be used, for example to assist in constructing a single delivery/collection probe, which could be hand-held. Such a probe, connected by fibre optic links to a laser light source and to a spectral detector/analyser would be particularly convenient for rapid screening of bottles or other containers, for example in a security screening operation such as an airport, or in checking for counterfeit or otherwise sought beverage bottles or other containers in a manufacture, distribution or retail environment.

In particular, the invention provides a method of screening unknown contents within a container, and especially within a plurality of such containers, to determine one or more characteristics of the contents, comprising:

directing a probe light beam (or beams) through a wall of said container and through said contents to a sample region (or regions) within said contents, the intersection of said probe light beam and the wall defining a delivery region (or regions);

collecting light scattered out of said beam within said sample region along a collection path not containing said delivery region;

detecting one or more Raman spectral features of said collected light; and analysing said one or more Raman spectral features to determine said characteristics.

The delivery region of said container wall is preferably at least semi-transparent, or sufficiently transparent to said light beam, to permit continuation of a substantial part of said probe light beam to said sample region within the contents. Similarly, the contents are preferably at least semi-transparent, or sufficiently transparent, to said light beam, to permit continuation of a substantial part of said probe light beam from said delivery region to said sample region.

In particular, the method is advantageous when used with containers having walls which exhibit strong Raman scattering and/or fluorescence, such as silica glass or a polymer plastic. The method is suitable, for example, for with contents materials such as liquids and gels, for example liquid or gel cosmetics, medicaments and beverages. Typically, the method may be used to detect characteristics of explosives, ingredients for explosives, alcohols and toxins within container contents.

The invention also provides apparatus corresponding to the above methods, for example a screening probe for determining characteristics of the unknown contents of a container, comprising optics arranged to deliver a probe light beam into said contents, through a first region of the container wall, and to collect light scattered out of the beam within the contents, through a second region of the container wall substantially separate, spaced from or not intersecting with the first region.

In particular, the invention provides apparatus for screening the contents of containers for specified characteristics comprising:

delivery optics arranged to direct a probe light beam through a wall of a said container and through said contents to a sample region within said contents, the intersection of said probe light beam and the wall defining a delivery region;

collection optics arranged to collect light scattered out of said beam within said sample region along a collection path or beam substantially not containing or intersecting said delivery region; and a spectral analyser adapted to detect one or more Raman spectral features of said collected light.

The apparatus may typically further comprising a data processing unit adapted to determine said specified characteristics from said one or more detected Raman spectral features, such as those mentioned above.

Conveniently, the optics to direct a probe light beam into the container and to collect light scattered out of the beam within the sample region may be provided as a common delivery/collection probe, for example a hand held probe suitable for use in security and other screening operations.

The invention is relevant to containers and contents in which the probe light beam, or a substantial part of the beam propagates through the container wall and the contents to the sample region. For this to happen, the path length of the beam through the container wall, and the path lengths thereafter within the contents to the sample region should both be less, and preferably much less than (such as less than 20% of) the relevant photon propagation distance, t, over which a photon direction is fully randomised. This distance is termed the transport length of the scattering medium ($l_t$), with the scattering medium either being the container wall or the contents. The transport length is typically an order of magnitude longer than the mean free scattering length $l_s$ of photons in the medium. The mathematical relationship is $l_s=(1-g)l_t$, where g is the anisotropy for an individual scattering event. Imaging within a medium is possible on distances shorter than the transport length $l_t$. Clearly, the collection path of the photons scattered out of the beam within the sample region and which are thereafter collected by the collection optics is subject to the same constraints.

Transport lengths within scattering media are discussed in Brenan C. J. H and Hunter I. W., J. Raman Spectroscopy 27, p 561 (1996), and in Das B. B., Liu F. and Alfano R. R., Rep. Prog. Phys. 60, p 227 (1997).

BRIEF DESCRIPTION OF THE DRAWINGS

Embodiments of the invention will now be described, by way of example only, with reference to the drawings, of which:

FIGS. 4a to 4e illustrate various other configurations of the probe light beam or beams (stippled) and collection path or paths (shaded) at the wall of the container further to the basic point laser beam delivery system shown in FIG. 1;

FIGS. 8a-8c relate to similar experiments using a plastic Highland Spring® mineral water bottle containing either the mineral water product or methanol.

DETAILED DESCRIPTION OF PREFERRED EMBODIMENTS

Figure 1:
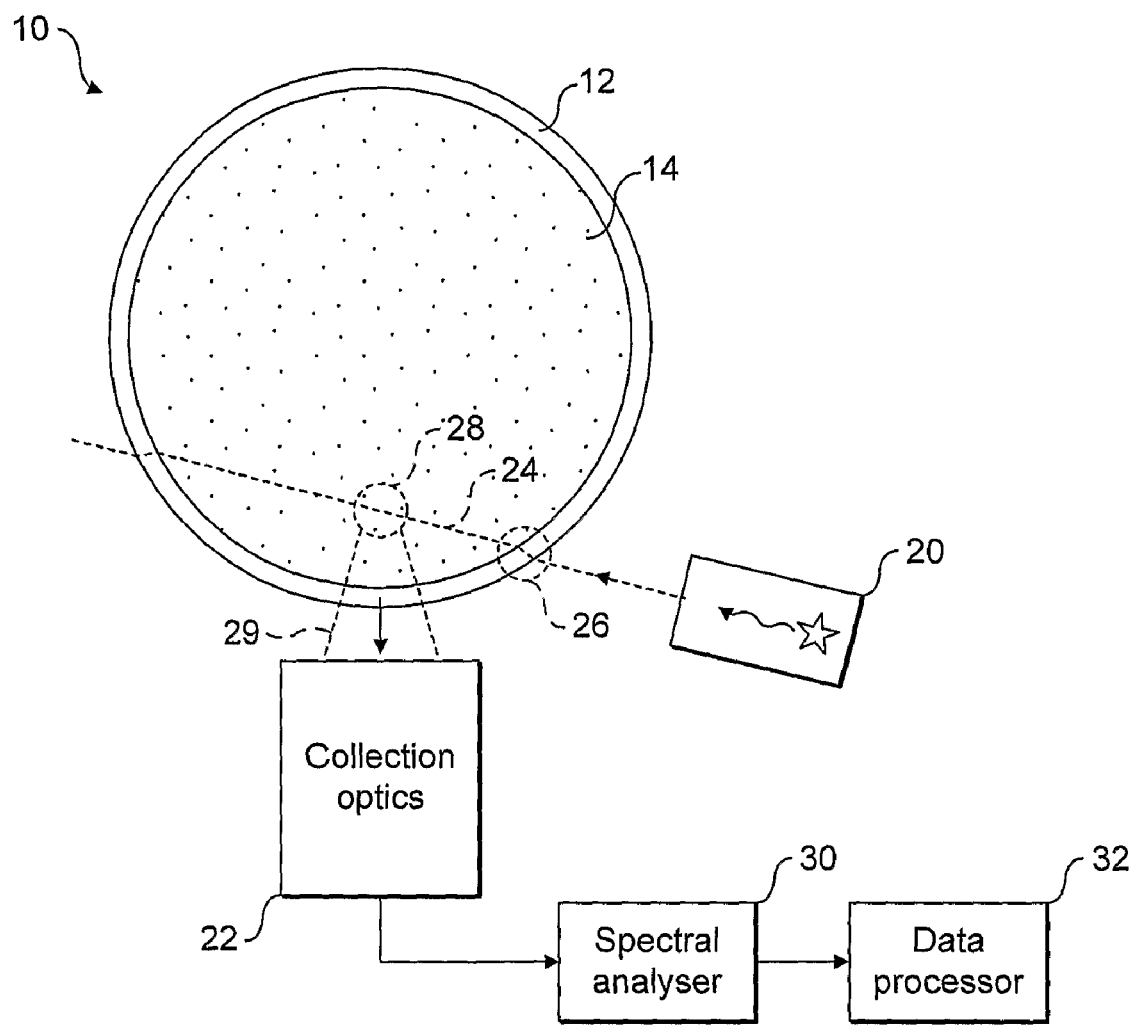
FIG. 1 illustrates the transmission of a probe light beam into the contents of a container, and detection of Raman spectral features in light scattered from the beam into a collection optical path, according to an embodiment of the invention.

Referring now to FIG. 1 there is shown, schematically, a container 10 having a container wall 12 which encloses container contents 14. Probe optics, shown here as separate delivery optics 20 and collection optics 22, serve to direct a laser light beam 24 through the container wall and into the contents 14. A small proportion of the photons of the laser beam are Raman scattered throughout the volume and length of the laser beam as it passes through the container wall 12, through the contents 12, and typically through the container wall again. Two regions of Raman scattering of particular note are a delivery region 26 of container wall illuminated directly by the laser beam as it enters the container 10, and a sample region 28 within the contents, from which the collection optics 22 collects scattered light along a collection optical path 29.

A spectral analyser 30 coupled to the collection optics is used to measure one or more Raman spectral features of the scattered light collected from the sample region 28. Measurements of Raman spectral features made by the spectral analyser 30 may be communicated to a data processor 32 which uses the measurements to provide indications of the nature of the contents 14 within the container.

The probe optics may take a variety of forms, for example as discussed in particular examples below. In particular, the laser beam and/or the collection optical path may be divided into plural separate beams or paths, and concentric ring, line and other geometries may be used.

The laser beam may typically be provided by a quasi-monochromatic laser such as a single-line continuous wave diode laser operating at 830 nm, with a power of around 100 mW directed to the delivery region 26. The collection optics may use a focal arrangement to optimise collection of scattered light from the sample region 28, for example having one or more focal points or focal regions coincident with the sample region 28. The spectral analyser may take a variety of forms for example using one or more filters, or a conventional or Fourier transform spectrograph to isolate Raman features of interest.

The container wall 12 may typically exhibit much stronger Raman scattering per unit volume than the contents, and typically also considerable fluorescence. As illustrated therefore, the probe optics are arranged such that the delivery region 26 of the container wall does not lie within the direct optical path between the sample region 28 and the collection optics 22. This configuration dramatically reduces contamination of the desired Raman signal of the contents 14 by undesired Raman signal and/or fluorescence of the container wall, thereby increasing sensitivity to the Raman signal of the contents 14.

The described arrangement may be used to determine indications of the nature of the content of containers in a variety of contexts, such as the detection of: counterfeit alcoholic beverages; beverage content in a production environment; unauthorised contents in beverage, medicament, cosmetic or toiletries containers, such as potential explosives ingredients or other hazardous or poisonous materials, in an airport or other security environment.

The container wall 12 may therefore typically be made of a conventional silica glass or a plastic such as polyethylene or polypropylene. For the laser beam 24 to pass through the container wall 12 and into the contents 14 as a beam well enough formed to deliver sufficient photon intensity to the sample region 28, the container wall should be transparent or semi-transparent at the wavelength of the laser light, at least over an area suitable to be used as the delivery region, bearing in mind that there may be paper labels, printing and regions of different colours and opacities on the container wall. For the laser beam to pass through the contents as a beam again well enough formed to deliver sufficient photon intensity to the sample region 28, the contents should also be transparent or semi-transparent at the wavelength of the laser light. A strongly scattering contents 14 would also have the adverse effect of scattering the laser light to all parts of the container wall 12, increasing the Raman signal of the container wall in the light received by the collection optics and thereby reducing the sensitivity of the arrangement to the Raman signal of the contents 14.

The degree to which the probe beam may be scattered within the container wall and the contents will vary depending on the nature of the materials involved. For example, the unscattered probe beam may retain close to 100% of its intensity when reaching the sample region in a clear plastic bottle of water, while retaining only perhaps 30% when passing through a coloured bottle containing a moderately turbid fruit juice. If the beam loses more intensity into scattering, especially elastic scattering within the container wall and contents, the intensity of unscattered beam photons and photons scattered elastically from the beam, in combination within the sample region, is likely to be less. However, a larger volume of the container contents will be illuminated by the incident light, contributing to Raman scattering over a larger volume. Raman photons will themselves be elastically scattered within the content and some proportion of these will consequently pass back through the wall of the container and be received by the collector optics. The large volume of the content, and the spacing between the delivery region on the container wall and the optical collection path ensure that the Raman signature continues to be heavily weighted toward the content, with little contribution from the container wall. Embodiments of the present invention therefore accommodate increasing scattering or turbidity within samples without serious loss of function.

Specific Arrangements

Figure 2:
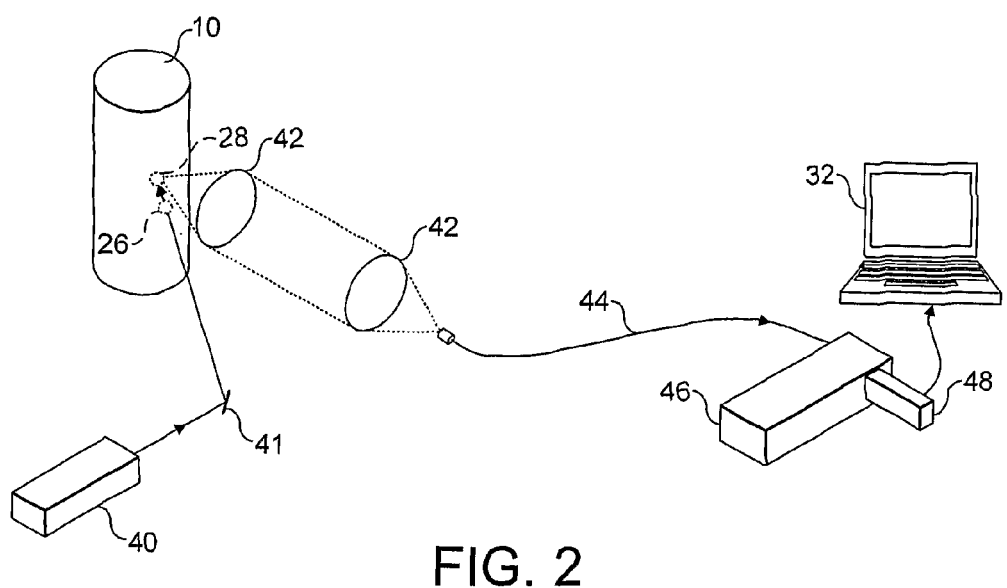
FIG. 2 illustrates a first scheme for putting the arrangement of FIG. 1 into effect.
Figure 3:
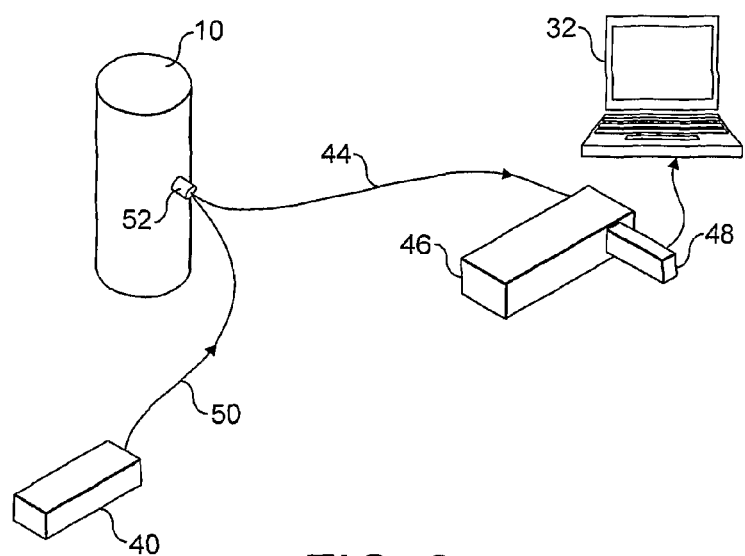
FIG. 3 illustrates a second scheme for putting the arrangement of FIG. 1 into effect.

FIGS. 2 and 3 illustrate some ways in which the arrangement of FIG. 1 may be put into effect, in slightly more detail and using like reference numerals where appropriate. Referring to FIG. 2, the container 10 is provided by a glass or plastic drinks bottle. The delivery optics 20 to deliver the laser light into the container at a delivery region 26 is provided by a system of one or more mirrors 41, and a laser unit 40 providing the laser beam is also shown. The Raman signal scattered within the bottle contents is collected by collection optics 20 provided as imaging optics 42, which receive scattered light from the sample region 28 within the contents of the container, along an optical path which does not include the delivery region. The imaging optics feed into a collection fibre optic bundle 44 for delivery to spectrometer 46. The spectrometer presents a spectrum onto a CCD pixel array 48, and data from the imaged spectrum is delivered to a data processor 32 provided by a personal computer or similar.

In the arrangement of FIG. 3 the laser beam is delivered from the laser unit 40 using a delivery fibre optic bundle 50 to a combined delivery/collection probe head which both delivers the laser light into the container 10 through one or more delivery regions 26, and collects scattered light from the sample region within the container along one or more optical paths which do not include the one or more delivery regions. As for FIG. 2, the collected light is delivered to a spectrometer 46 by a delivery fibre optic bundle 44.

Delivery and Collection Geometries

FIGS. 4a to 4e illustrate a variety of other ways, in addition to the basic point delivery system shown in FIG. 1, in which the laser light may be delivered into the container 10 and collected through the container, especially when using a combined delivery/collection probe head as shown in FIG. 3. The delivery region or regions 26 of the container wall 12 when the probe is brought close to the container wall are in each case shown stippled, and the intersection of the collection optical path from the sample region 28 to the collection optics 22 is shown shaded.

In FIG. 4a a single ring beam of laser light is delivered into the container, and the single collection optical path is concentric within this ring. To avoid the laser beam focussing to a point, which could burn some targets, a phase aberrator could be inserted into the laser beam to distort the laser beam profile slightly.

In the similar arrangement of FIG. 4b the ring beam of FIG. 4a is broken into two arcuate ring segments. Of course, different numbers of segments with different shapes could be used, and in FIG. 4c six circular delivery regions 26 are shown equally spaced around a central circular collection optical path 29. Finally, in FIG. 4d there are provided two parallel rectilinear delivery regions of the same length, with a circular collection optical path spaced centrally between.

FIG. 4e shows an arrangement in which a laser beam is delivered through a central delivery region 26, and the collection optical path 29 at the container wall 12 forms a ring (or alternatively segments of a ring or other multiple regions similar to those of FIGS. 4a to 4d).

Figure 5A:
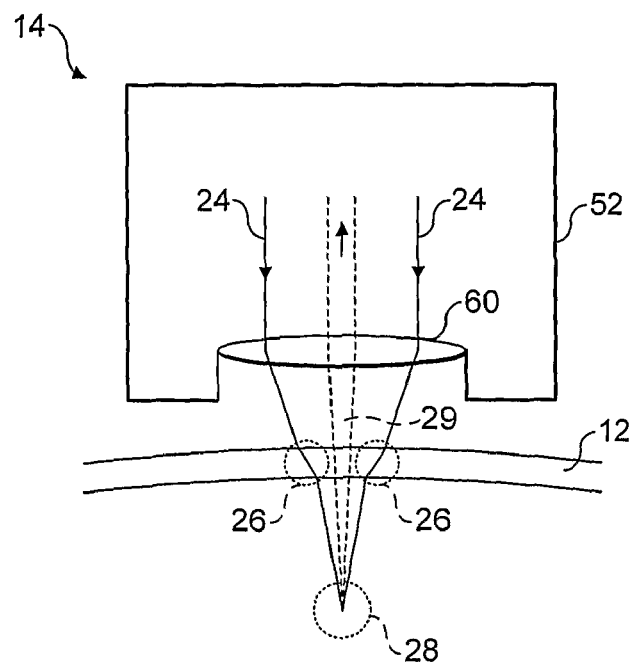
FIGS. 5a and 5b show optical arrangements suitable for providing a concentric configuration of the probe light beam or beams and collection path or paths using a lens (FIG. 5a) and a double axicon arrangement (FIG. 5b)
Figure 5B:
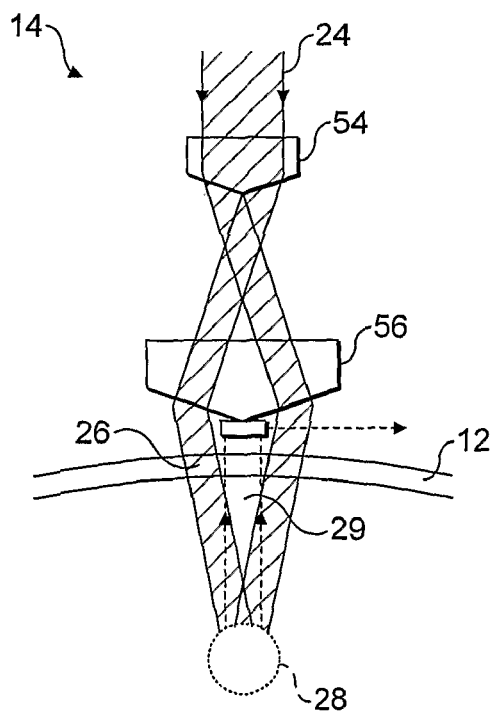

A combined delivery/collection probe head may be realised using optics such as those illustrated in FIGS. 5a and 5b. In FIG. 5a laser light is directed towards the sample region 28 by refraction towards the periphery of a lens 60 forming part of a combined delivery/collection probe head 52. Light scattered from the sample region 28 is collected by a central region of the lens.

In FIG. 5b a broad laser beam 24 passes through two coaxial conical axicon lenses 54, 56, of different cone angles, to form a ring beam convergent on the sample region 28. A small prism or mirror in front of the centre of the second, larger axicon collects scattered light from the sample region 28 and redirects this light laterally away from the axicon axis. To form line segment delivery regions as shown in FIG. 4d, a similar arrangement using triangular prisms may be used.

Experiments

An embodiment of the invention was used to obtain Raman intensity spectra on a variety of samples, including commercial plastic beverage bottles sold containing the Lilt® soft drink, and as an alternative containing methanol, and on a bottle sold containing Highland Spring® mineral water, and again as an alternative containing methanol. The experimental set up was as follows. The spectra were obtained using a 55 mW continuous wave laser beam generated from a temperature stabilised diode laser operating at 827 nm. The beam was spectrally purified by removing any residual amplified spontaneous emission components from its spectrum using two 830 nm bandpass filters. The beam was weakly focused onto the bottle surface to about 1 mm diameter spotsize. The point of incidence of the laser beam on the bottle surface was displaced from the Raman collection pathway intersection with the bottle surface by about 5-7 mm.

The Raman light was collected in backscattering mode using a 1.2 f-number lens from a depth of several millimetres within the bottle. The scattered light was imaged, with magnification 1:1, onto the front face of a fibre probe. A combination of notch and edge filters was used to suppress the elastically scattered component of light. The fibre probe consisted of 22 fibres collecting Raman signal. The Raman light was then propagated through the fibre system of a length of about 2 m to a linear fibre end oriented vertically and placed in the input image plane of a Kaiser Optical Technologies Holospec spectrograph (f#=1.8i).

The Raman spectra were collected using a NIR back-illuminated deep depletion TE cooled CCD camera (Andor Technology, DU420A-BR-DD, 1024×256 pixels) by binning all the fibres into one Raman spectrum. The Raman spectra measured in the conventional geometry in which the laser delivery and Raman collection regions intersect on the bottle surface was collected by reducing the displacement between the collection and deposition points on the surface of the bottle from 7 mm to zero. This was accomplished merely by redirecting the laser beam to the new position. The other parameters of the system remained unchanged. The overall acquisition time for all the spectra was 10 s.

Figure 6A:
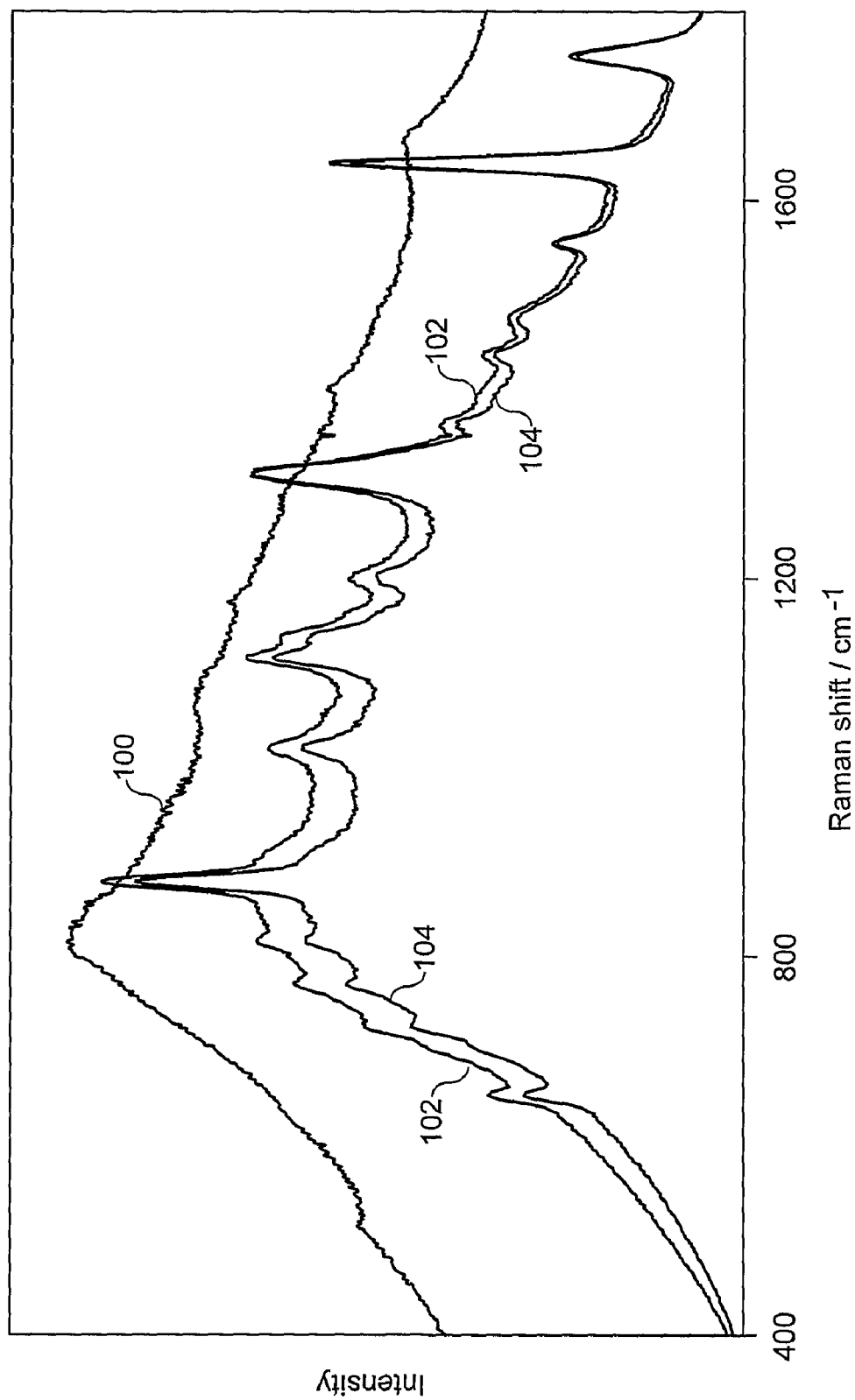
FIG. 6a is a plot of Raman spectral intensity measured in an arrangement in which the collection beam or optical path from a region of scattering intersects the probe light beam at wall of a Lilt® plastic soft drink bottle: curve 100 is for the soft drink alone, curve 104 is from an empty bottle, and curve 102 is from a bottle containing the drink.

The Raman intensity spectra from using the conventional arrangement, in which the collection pathway contains the delivery region, for Lilt® plastic drinks bottle containing Lilt soft drink are shown in FIG. 6a. The vertical scale is adjusted separately for each spectrum to bring the curves into similar scales. The relatively smooth top curve 100 shows the spectrum for the Lilt drink without a container wall present. The spectrum of the container wall alone is shown as the lowest curve 104, and the container wall with the Lilt drink present in the container is shown as the curve which is very similar, but slightly above the container curve. Clearly, drink characteristics of curve 102 are largely swamped by characteristics of the plastic bottle itself.

Figure 6B:
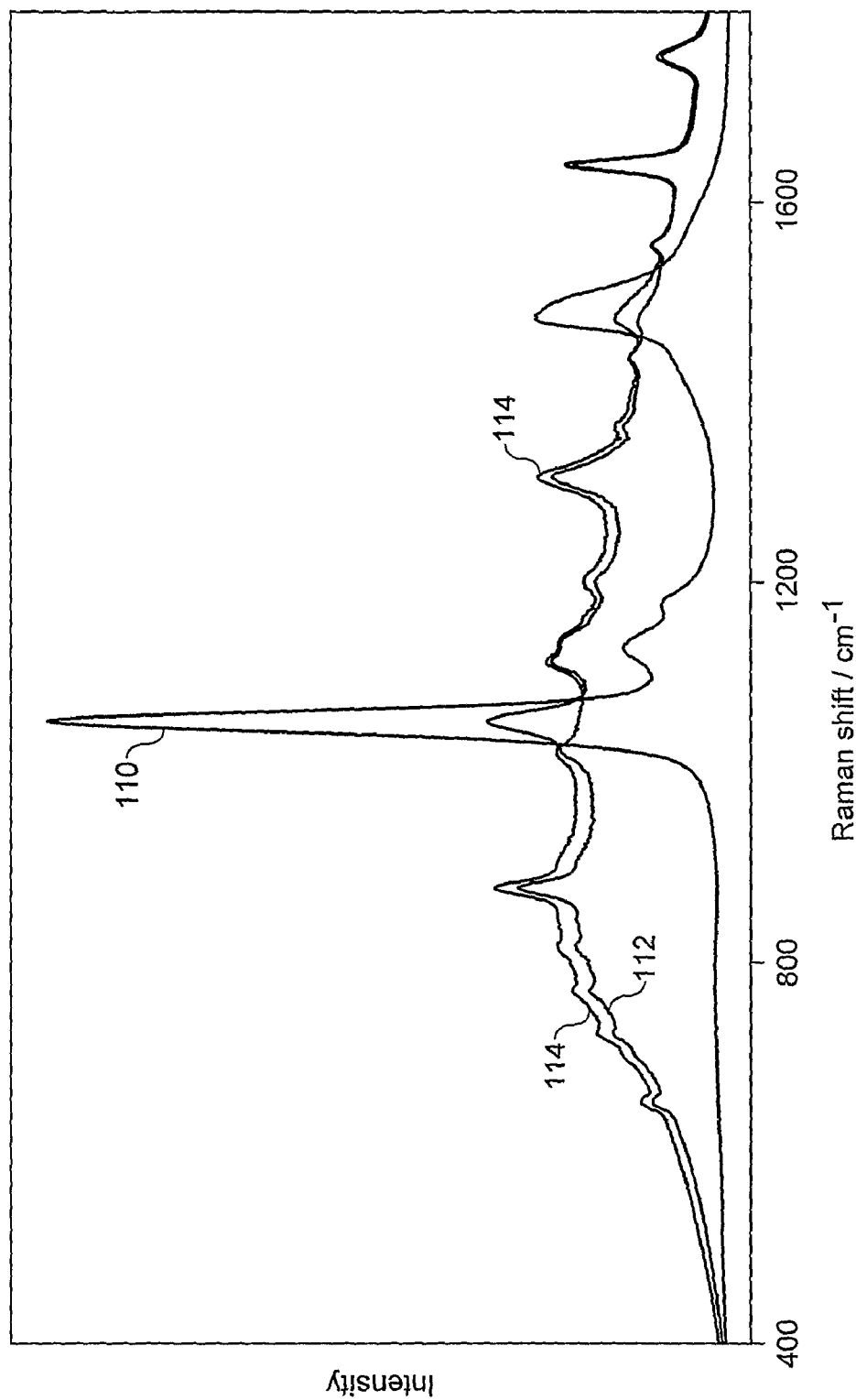
FIG. 6b corresponds to FIG. 6a, but using methanol instead of the Lilt® soft drink.

FIG. 6b corresponds to FIG. 6a, but with the Lilt soft drink substituted by methanol. The pure methanol spectrum is shown as relatively smooth curve 110. The spectrum for methanol in the Lilt bottle is shown as curve 114 which is only slightly different to the spectrum 112 for the bottle alone.

Figure 7A:
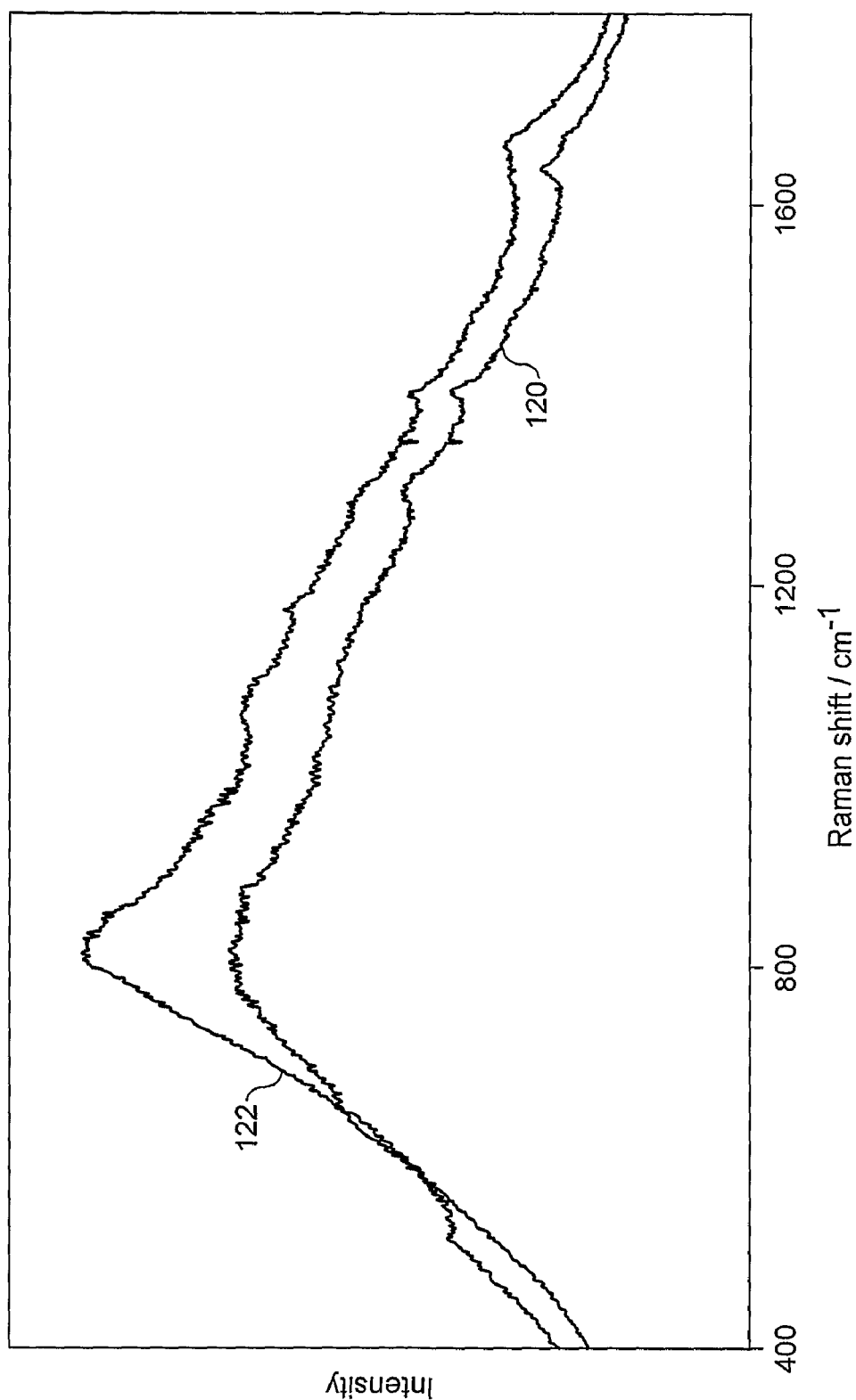
FIG. 7a is a plot of Raman spectral intensity measured in an arrangement in which the collection beam does not intersect the probe light beam at the container wall of the Lilt® plastic soft drink bottle of FIGS. 6a and 6b: curve 120 is for the soft drink alone, and curve 122 is for the soft drink within the bottle.
Figure 7B:
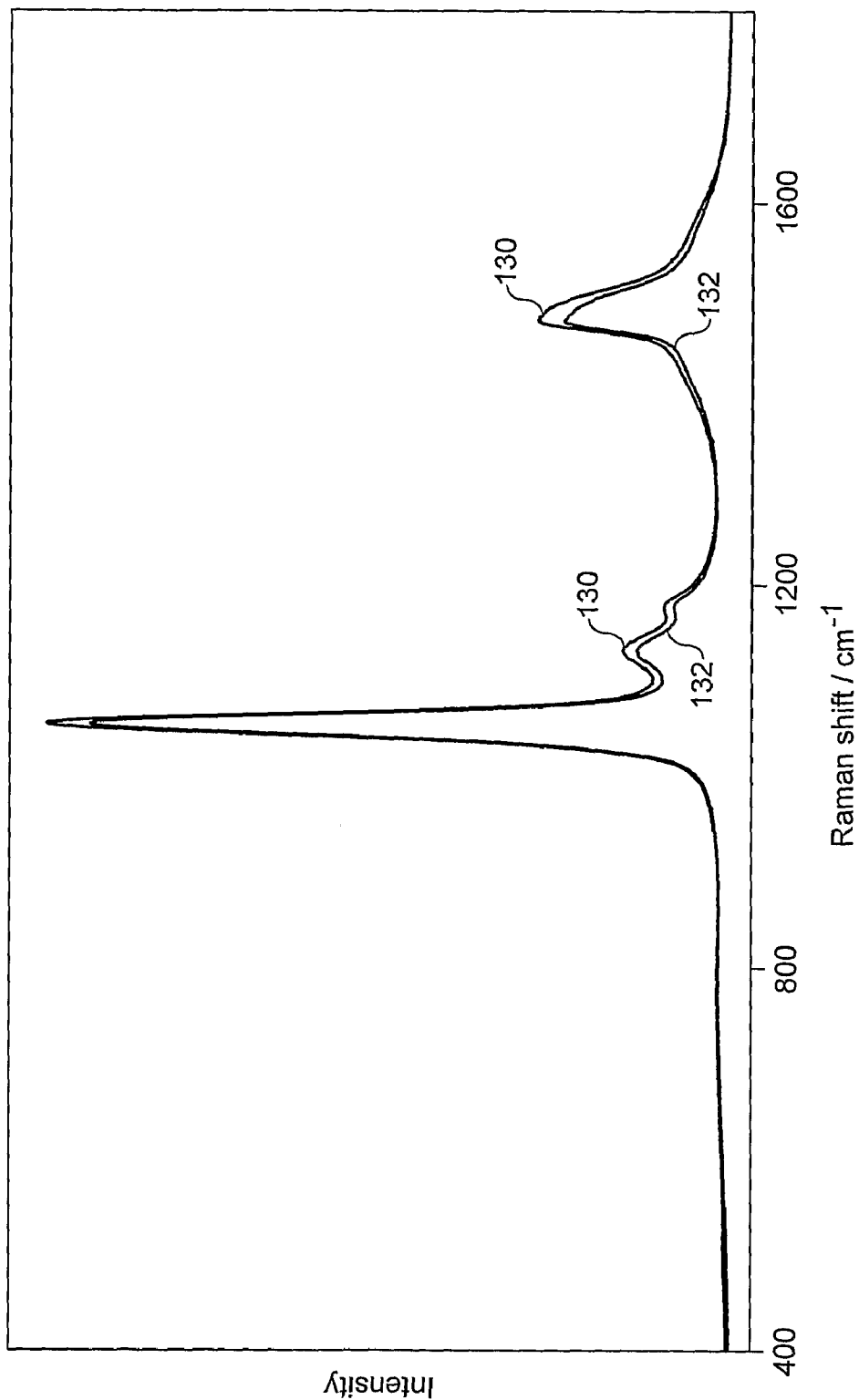
FIG. 7b corresponds to FIG. 7a, but using methanol in place of the Lilt® soft drink.

The corresponding Raman intensity spectra from using the arrangement according to the invention, in which the collection pathway is spaced from and does not contain the delivery region, are shown in FIGS. 7a and 7b. The slightly smoother lower curve 120 of FIG. 7a shows the spectrum for the Lilt drink without a container wall present. The spectrum of the container wall with the Lilt drink present in the container is shown as the curve 122 which is very similar, but slightly above the pure drink curve. Clearly, using the optical geometry of the invention the Raman spectrum of the drink behind the container wall is very close to that of the drink with no intervening wall. In FIG. 7b, the pure methanol spectrum 130 and the spectrum of methanol within the plastic Lilt bottle 132 are almost indistinguishable, with spectral features of the plastic bottle itself being almost eliminated.

Returning to the conventional Raman technique in which the delivery region interferes with the collection path, the lower, relatively featureless curve 140 of FIG. 8a is a Raman spectrum of water. Water exhibits a more complex Raman signature only at rather higher frequencies. The more complex upper curves are the spectrum of a Highland Spring® plastic mineral water bottle 144, and that of the bottle including its water contents. It is clear that using the conventional technique the water signature is overwhelmed by the signature of the plastic bottle.

Figure 8B:
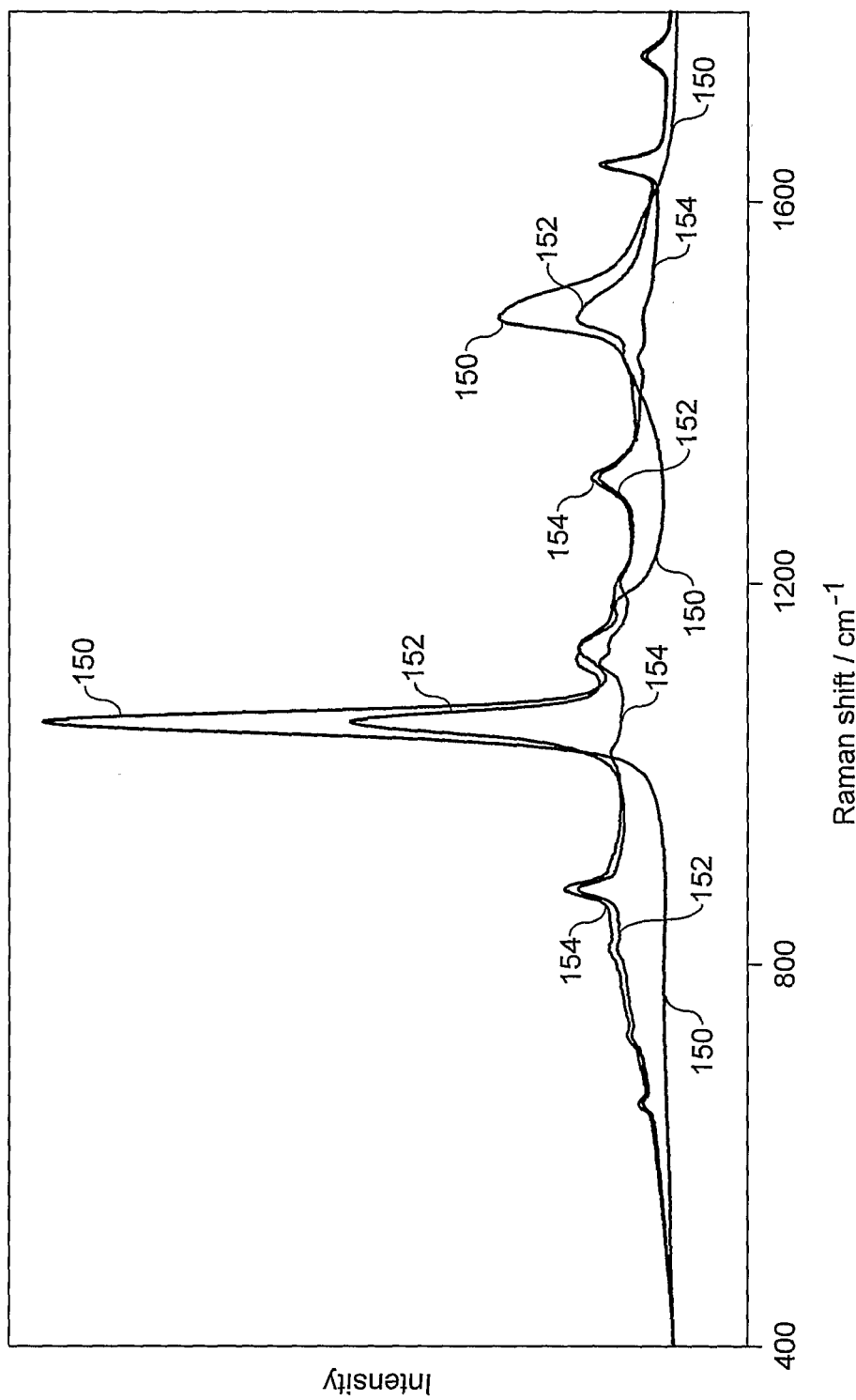
Figure 8C:
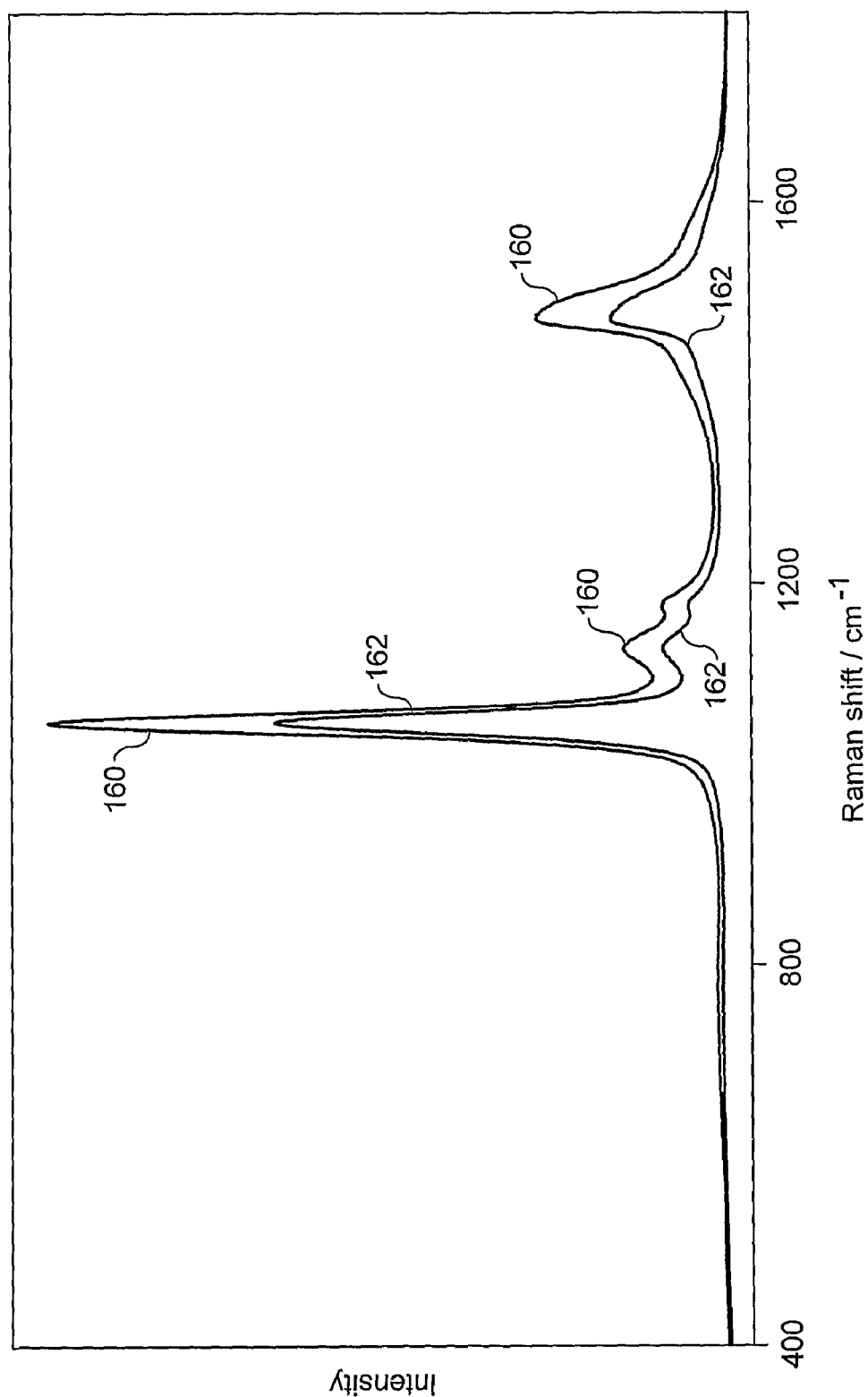

To obtain the spectra of FIG. 8b the same mineral water bottle was filled with methanol, and was again tested using the conventional arrangement. The signature of methanol on its own is shown as the smoother curve 150 with the highest peak. The main methanol peak is apparent in the curve 152 of methanol behind the container wall, but generally this curve and the curve 154 of the container alone are very similar. To obtain the spectra of FIG. 8c the same mineral water bottle filled with methanol was tested using the arrangement embodying the invention. Clearly, in this case, the curve for pure methanol 160 and the curve for methanol behind the plastic container wall are much more similar.

Although particular embodiments of the invention have been described in detail, it will be apparent to the skilled person that a variety of changes and modifications may be made to such embodiments without departing from the scope of the claims.

The invention claimed is:

1. A method of non-invasive security screening of unknown contents within a container to determine one or more characteristics of the contents, comprising:
    performing non-invasive security screening for a container containing unknown contents, said non-invasive screening of the container and its contents being performed without opening the container for said screening,
    said non-invasive screening comprising:
    directing a probe light beam through a wall of said container and through said contents to a sample region within said contents, the intersection of said probe light beam and the wall defining a delivery region;
    collecting light scattered out of said beam within said sample region along a collection path not containing said delivery region;
    detecting one or more Raman spectral features of said collected light; and
    analyzing said one or more Raman spectral features to determine said one or more characteristics of said unknown contents,
    wherein in said collected light, spectral characteristics of said unknown contents are stronger than spectral characteristics of the container, and
    wherein spectral characteristics of the container are stronger than spectral characteristics of said unknown contents in light that is scattered out of said beam within said contents, along a path containing said delivery region.

2. The method of claim 1 wherein at least the delivery region of said container wall is transparent, or sufficiently transparent, to said light beam, to permit continuation of said probe light beam to said sample region.

3. The method of claim 1 wherein the contents are transparent, or sufficiently transparent, to said light beam, to permit continuation of said probe light beam from said delivery region to said sample region.

4. The method of claim 1 wherein the container wall is comprised of a material selected from: silica glass; and plastic.

5. The method of claim 1 wherein the contents are comprised of a material selected from: a liquid; a gel; a cosmetic; a medicament; and a beverage.

6. The method of claim 1 wherein the characteristics are characteristics of one or more of: explosives; ingredients for explosives; alcohols; and toxins.

7. The method of claim 1 wherein said collecting comprises using collection optics having a focal region coincident with said sample region to collect said light scattered out of the probe beam in said sample region and into said collection path.

8. The method of claim 1 wherein the probe light beam is directed through the container wall, and the probe beam light scattered within the sample region is collected, by a common delivery/collection probe.

9. The method of claim 1 wherein the delivery region and the collection path are concentric.

10. The method of claim 9 wherein the delivery region is in a continuous or broken ring form around a central collection path form.

11. The method of claim 10 wherein the continuous or broken ring form is created using a double axicon arrangement, and the central form is coupled away from the sample region using an optical component positioned between the double axicon arrangement and the container wall.

12. The method of claim 10 wherein the continuous or broken ring form is optically constructed using the periphery of a lens, and the central form is coupled away from the sample region using a central region of the lens.

13. The method of claim 9 wherein the collection path at the container wall is in a continuous or broken ring form around a central delivery region form.

14. The method of claim 13 wherein the continuous or broken ring form is created using a double axicon arrangement, and the central form is coupled away from the sample region using an optical component positioned between the double axicon arrangement and the container wall.

15. The method of claim 13 wherein the continuous or broken ring form is optically constructed using the periphery of a lens, and the central form is coupled away from the sample region using a central region of the lens.

16. A method of security screening personal effects of passengers at airports, comprising carrying out the method of claim 1 on containers intended for carriage onto aircraft by said passengers.

17. A method of security screening the contents of containers such as bottles for unauthorised substances, comprising carrying out the method of claim 1 on said containers.

18. The method of claim 1, wherein the container containing the unknown contents is sealed, and the method screens the contents without opening the container.

19. The method of claim 1, wherein the container containing the unknown contents is closed such that the contents are not directly accessible from the outside, and the method screens the contents enclosed therein.

20. The method of claim 1, wherein said screening is a non-invasive security screening of the container and its unknown contents because the container is not opened for said screening.

21. The method of claim 1, wherein said method performs said non-invasive security screening of the container and its unknown contents without directly accessing the interior of the container and the contents, for said screening.

22. A method of non-invasive security probing of the contents of a container having a wall, comprising:
performing non-invasive security screening for a container containing contents, said non-invasive screening of the container and its contents being performed without opening the container for said screening,
said non-invasive screening comprising:
directing a probe light beam through the container wall into the contents;
collecting light scattered out of the probe light beam within the contents; and
detecting Raman spectral features in the collected light to determine characteristics of the contents,
wherein the light scattered out of the probe beam is collected along an optical pathway or beam which passes through a different part of the container wall than the probe beam,
wherein in said collected light, spectral characteristics of said contents are stronger than spectral characteristics of the container, and
wherein, along a path containing the probe light beam delivery region into the container, spectral characteristics of the container are stronger than spectral characteristics of said contents in light that is scattered out of said beam within said contents.

23. The apparatus of claim 22 wherein the delivery optics and collections optics comprise one or more common optical components.

24. The apparatus of claim 22 wherein the delivery optics and collection optics are arranged such that the probe light beam and the collection path are concentric, with one forming a peripheral feature and one forming a central feature.

25. The apparatus of claim 24 further comprising a double axicon arrangement adapted to form the peripheral feature, and a central optical element positioned in front of the double axicon arrangement so as to couple the central feature away from the axis of the double axicon arrangement.

26. The apparatus of claim 24 further comprising a lens having a peripheral region arranged to form the peripheral feature and a central region arranged to form the central feature.

27. The method of claim 22, wherein the container containing the contents is closed such that the contents are not directly accessible from the outside, and the method probes the contents enclosed therein without directly accessing the contents.

28. The method of claim 22, wherein said screening is a non-invasive security screening of the container and its contents because the container is not opened for said screening.

29. The method of claim 22, wherein said method performs said non-invasive security screening of the container and its contents without directly accessing the interior of the container and the contents, for said screening.

30. Apparatus for non-invasive security screening of the contents of containers for specified characteristics, comprising:
delivery optics arranged to direct a probe light beam through a wall of a container and through said contents to a sample region within said contents, the intersection of said probe light beam and the wall defining a delivery region;

collection optics arranged to collect light scattered out of said beam within said sample region along a collection path not containing said delivery region; and a spectral analyser adapted to detect one or more Raman spectral features of said collected light to determine one or more characteristics of said contents, thereby performing non-invasive security screening for the container containing said contents, said non-invasive screening of the container and its contents being performed without opening the container for said screening, wherein in said collected light, spectral characteristics of said contents are stronger than spectral characteristics of the container, and wherein spectral characteristics of the container are stronger than spectral characteristics of said contents in light that is scattered out of said beam within said contents, along a path containing said delivery region.

31. The apparatus of claim 30 further comprising a data processing unit adapted to determine said specified characteristics from said one or more detected Raman spectral features.

32. The apparatus of claim 30 wherein the collection optics have a focal region arranged to be coincident with a said sample region within a said container.

33. The apparatus of claim 30 wherein the optics to direct a probe light beam and to collect light scattered out of the beam within the sample region are provided as a common delivery/collection probe.

34. The apparatus of claim 33 wherein the probe is coupled to a laser by a fibre optic pathway for delivery of the probe light beam to the probe.

35. The apparatus of claim 30, wherein the container containing the contents is closed such that the contents are not directly accessible from the outside.

36. The apparatus of claim 30, wherein said screening is a non-invasive security screening of the container and its contents because the container is not opened for said screening.

37. The apparatus of claim 30, wherein said apparatus performs said non-invasive security screening of the container and its contents without directly accessing the interior of the container and the contents, for said screening.

38. A screening probe for determining characteristics of the contents of a container through non-invasive security screening, comprising optics arranged to deliver a probe light beam into said contents, through a first region of the container wall, and to collect light scattered out of the beam within the contents, through a second region of the container wall substantially separate, spaced from or not intersecting with the first region, wherein said collected light is used to perform non-invasive security screening for the container containing said contents, by determining one or more characteristics of said contents, said non-invasive security screening of the container and said contents of the container being performed without opening the container for said screening, wherein in said collected light, spectral characteristics of said contents are stronger than spectral characteristics of the container, and wherein spectral characteristics of the container are stronger than spectral characteristics of said contents in light that is scattered out of said beam within said contents, along a path containing said first region.

39. The screening probe of claim 38 wherein the optics are adapted to collect said scattered light by imaging a region of the beam within the contents.

40. The screening probe of claim 38 wherein the probe is adapted to be handheld.

41. A system comprising the screening probe of claim 38 and further comprising a spectral analyser arranged to receive said collected light from said probe, to analyse said collected light, and to detect one or more Raman spectral characteristics of said contents.

42. The system of claim 41 further comprising a data processor arranged to receive from said spectral analyser data relating to said one or more spectral features and to generate therefrom data descriptive of said contents.

43. The screening probe of claim 38, wherein the container containing the contents is closed such that the contents are not directly accessible from the outside.

44. The screening probe of claim 38, wherein said screening by said screening probe is a non-invasive security screening of the container and its contents because the container is not opened for said screening.

45. The screening probe of claim 38, wherein said screening probe performs said non-invasive security screening of the container and its contents without directly accessing the interior of the container and the contents, for said screening.

* * * * *